US010349656B2

United States Patent
Dubost et al.

(10) Patent No.: US 10,349,656 B2
(45) Date of Patent: *Jul. 16, 2019

(54) DIFLUOROMETHYL-NICOTINIC-INDANYL CARBOXAMIDES

(71) Applicant: BAYER CROPSCIENCE AKTIENGESELLSCHAFT, Monheim am Rhein (DE)

(72) Inventors: Christophe Dubost, La tour de Salvagny (FR); Philipp Winter, Düsseldorf (DE); Marco Brünjes, Hattersheim am Main (DE); Mark James Ford, Wiesbaden-Breckenheim (DE); Ulrike Wachendorff-Neumann, Neuwied (DE); Cyril Montagne, Monheim am Rhein (DE); Jean-Pierre Vors, Sainte Foy les Lyon (DE); Stephane Brunet, St Andre de Corcy (FR); Philippe Rinolfi, Chatillon D Azergues (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 73 days.

This patent is subject to a terminal disclaimer.

(21) Appl. No.: 15/320,780

(22) PCT Filed: Jun. 22, 2015

(86) PCT No.: PCT/EP2015/063938
§ 371 (c)(1),
(2) Date: Dec. 21, 2016

(87) PCT Pub. No.: WO2015/197530
PCT Pub. Date: Dec. 30, 2015

(65) Prior Publication Data
US 2017/0150717 A1    Jun. 1, 2017

(30) Foreign Application Priority Data
Jun. 25, 2014 (EP) .................................... 14173934

(51) Int. Cl.
A01N 43/40 (2006.01)
C07D 213/82 (2006.01)

(52) U.S. Cl.
CPC ........... *A01N 43/40* (2013.01); *C07D 213/82* (2013.01)

(58) Field of Classification Search
CPC ..................................................... A01N 43/40
See application file for complete search history.

(56) References Cited

U.S. PATENT DOCUMENTS

2013/0029626 A1    11/2013   Benting et al.

FOREIGN PATENT DOCUMENTS

| EP | 0256503 A2 | 2/1988 | |
| WO | 9212970 A1 | 8/1992 | |
| WO | 2009/054742 A2 | 10/2008 | |
| WO | WO-2009054742 A2 * | 4/2009 | ........... C07D 213/80 |
| WO | 2010109301 A1 | 9/2010 | |
| WO | WO-2011162397 A1 * | 12/2011 | ............. A01N 43/56 |
| WO | 2012065947 A1 | 5/2012 | |
| WO | 2012084812 A1 | 6/2012 | |
| WO | WO-2014095675 A1 * | 6/2014 | ........... C07D 405/12 |

OTHER PUBLICATIONS

Wermuth C G "Molecular Variations Based on Isosteric Replacements"; Practice of Medicinal Chemistry (1996), pp. 203-237.
Erickson J A et al "Hydrogen Bond Donor Properties of the Difluoromethyl Group"; J. of Organic Chemistry (1995); pp. 1626-1631.
Masatsuga Oda Quantitative Structure-Activity Relationships of 2-Chloropyridine-3-carboxamide Fungicides; J. Pesticide sci. 18, (1993) pp. 49-57.
International Search Report of PCT/EP215/063938 dated Dec. 16, 2015.

* cited by examiner

*Primary Examiner* — Andrew D Kosar
*Assistant Examiner* — John S Kenyon
(74) *Attorney, Agent, or Firm* — McBee Moore Woodward & Vanik IP, LLC

(57) ABSTRACT

The present invention relates to novel difluoromethyl-nicotinic indanyl carboxamides, to processes for preparing these compounds, to compositions comprising these compounds, and to the use thereof as biologically active compounds, especially for control of harmful microorganisms in crop protection and in the protection of materials.

12 Claims, No Drawings

DIFLUOROMETHYL-NICOTINIC-INDANYL CARBOXAMIDES

CROSS REFERENCE TO RELATED APPLICATIONS

This application is a § 371 National State Application of PCT/EP2015/063938, filed Jun. 22, 2015, which claims priority to European Application No. 14173934.2 filed Jun. 25, 2014.

BACKGROUND OF THE INVENTION

Field of the Invention

The present invention relates to novel difluoromethyl-nicotinic indanyl carboxamides, to processes for preparing these compounds, to compositions comprising these compounds, and to the use thereof as biologically active compounds, especially for control of harmful microorganisms in crop protection and in the protection of materials.

Description of Related Art

It is already known that certain pyrazole indanyl carboxamides have fungicidal properties (e.g. WO 1992/12970, WO 2012/065947, J. Org. Chem. 1995, 60, 1626-1631 and WO 2012/084812).

It is also already known that certain pyridine indanyl or benzofuran carboxamides have fungicidal properties (e.g. EP-A 0 256 503, JP-A 1117864, JP-A 1211568, EP-A 315502, J. Pesticide sci. 18, 1993, 49-57, J. Pesticide sci. 18, 1993, 245-251).

It is also already known that certain benzoyl indanyl amides have fungicidal properties (WO 2010/109301).

Since the ecological and economic demands made on modern active ingredients, for example fungicides, are increasing constantly, for example with respect to activity spectrum, toxicity, selectivity, application rate, formation of residues and favorable manufacture, and there can also be problems, for example, with resistances, there is a constant need to develop novel fungicidal compositions which have advantages over the known compositions at least in some areas.

SUMMARY

This invention now provides novel difluoromethyl-nicotinic indanyl carboxamides of the formula (I)

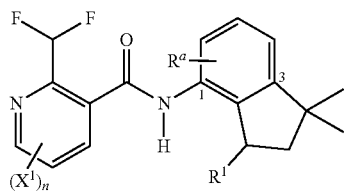

(I)

in which
$X^1$ represents fluorine, chlorine, bromine, methyl, ethyl, trifluoromethyl, difluoromethyl;
n represents 0 or 1;
$R^a$ represents represents hydrogen, fluorine, chlorine, bromine, methyl or trifluoromethyl;
$R^1$ represents ethyl, n-propyl, iso-propyl, iso-butyl.

Preferred are compounds of the formula (I) in which
$X^1$ represents fluorine and n represents 0 or 1, more preferably n represents 0;
$R^a$ represents represents hydrogen;
$R^1$ represents ethyl, n-propyl, iso-propyl, iso-butyl.

Most preferred among the preferred compounds of the formula (I) are the (−)-isomers ((−) is referring to the specific rotation).

Furthermore the invention provides compounds of the formula (III)

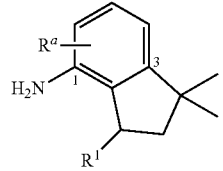

(III)

in which
the radicals $R^a$ and $R^1$ are as defined as for formula (I).

A further aspect of the present invention are compounds of the formula (IV),

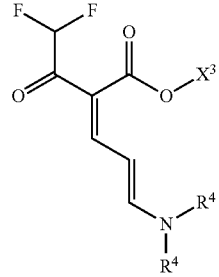

(IV)

in which
$X^3$ represents $C_1$-$C_6$ alkyl;
$R^4$ independently of one another represents $C_1$-$C_6$ alkyl.

DETAILED DESCRIPTION OF A PREFERRED EMBODIMENT

Preferred are compounds of the formula (IV) in which
$X^3$ represents ethyl, methyl;
$R^4$ independently of one another represents methyl, ethyl.

Most preferred is compound of the formula (IV) in which
$X^3$ represents ethyl;
$R^4$ represents ethyl.

Illustration of the Processes and Intermediates

Carboxamides of the formula (I) are obtained when acids of formula (II) are reacted with amines of formula (III) in the presence of a coupling agent, optionally in the presence of an acid binder and optionally in the presence of a diluent, Or by reacting compounds of formula (XII) with amines of formula (III) optionally in the presence of a coupling agent, optionally in the presence of an acid binder and optionally in the presence of a diluent (see Process (a)):

Process (a):

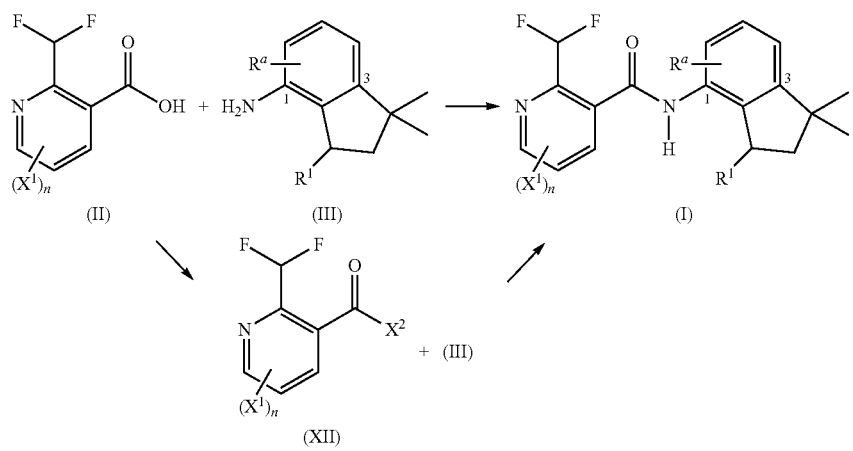

In formula (II), $X^1$ and n have generally and preferably those meanings which have already been mentioned for these radicals in connection with the description of the compounds of the formula (I).

In formula (XII), $X^2$ represents halogen. $X^2$ preferably represents fluorine, chlorine, particularly preferably chlorine. $X^1$ and n have generally and preferably those meanings which have already been mentioned for these radicals in connection with the description of the compounds of the formula (I).

The formula (III) provides a general definition of the amines required as starting materials for carrying out the Process (a) according to the invention.

In this formula (III), $R^a$, $R^1$, $R^2$, $R^3$ have generally, preferably, particularly preferably, very particularly preferably those meanings which have already been mentioned for these radicals in connection with the description of the compounds of the formula (I).

Compounds of formula (XII) are obtained by reacting compounds of formula (II) with halogenating agents such as, for example, thionyl chloride, thionyl bromide, oxalyl chloride, phosgene or $POCl_3$ Compounds of formula (II) used as starting materials are obtained by saponification of esters of formula (XIII) optionally in the presence of a diluent (see Process (b)) using methods described in the literature:

Process (b):

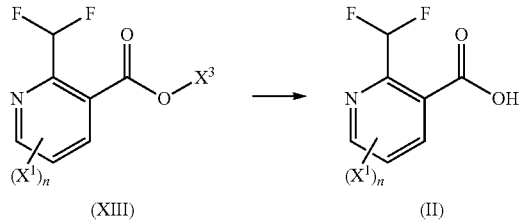

In formula (XIII), $X^1$ and n have generally and preferably those meanings which have already been mentioned for these radicals in connection with the description of the compounds of the formula (I). $X^3$ represents a $C_1$-$C_6$ alkyl group.

Compounds of formula (XIII) used as starting materials are commercially available or prepared using similar procedures to the ones described in *Chem. Commun.*, 2008, 4207-4209.

Compounds of formula (II-a), compounds of formula (II) wherein n represents 0, are obtained by reacting compounds of formula (IV) ammonia as a gas or dissolved in a suitable solvent, e.g. in water as ammonium hydroxide optionally in the presence of a diluent (see Process (c)):

Process (c):

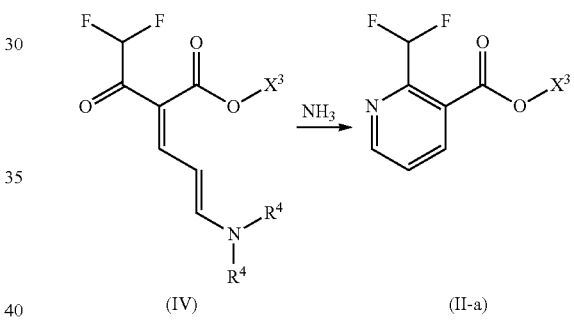

In formula (IV), $X^3$ and $R^4$ independently represent $C_1$-$C_6$ alkyl groups. Formula (IV) represents both the E and the Z isomers, any mixtures of these isomers, and the possible tautomeric forms.

Compounds of formula (IV) used as starting materials are obtained by reacting compounds of formula (V) with Vilsmeier salts of formula (VI) and compounds of formula (VII) optionally in the presence of a diluent (see Process (d)):

Process (d):

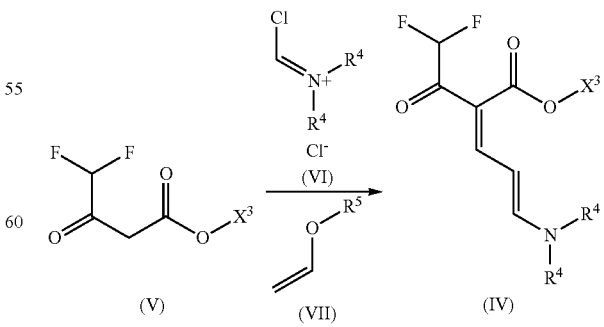

In formula (V), $X^3$ represents a $C_1$-$C_6$ alkyl group; preferably methyl and ethyl; most preferably ethyl.

In formula (VI), $R^4$ represents a $C_1$-$C_6$ alkyl group; preferably methyl and ethyl; most preferably ethyl.

In formula (VII), $R^5$ represents a $C_1$-$C_6$ alkyl group; preferably methyl and ethyl; most preferably methyl.

Vilsmeier salts of formula (VI) can be prepared separately or in-situ prior to the reaction, by reacting the corresponding formamide with an activating agent such as, for example, $SOCl_2$, $POCl_3$, Oxalylchloride or phosogene.

Compounds of Formula (VII) are commercially available.

Compounds of formula (IV) can also be obtained by reacting compounds of formula (V) with aldehydes of formula (VIII) in the presence of a dehydrating agent such as, for example, acetic anhydride or sulfuric acid and optionally in the presence of a diluent (Process (e)):

Process (e):

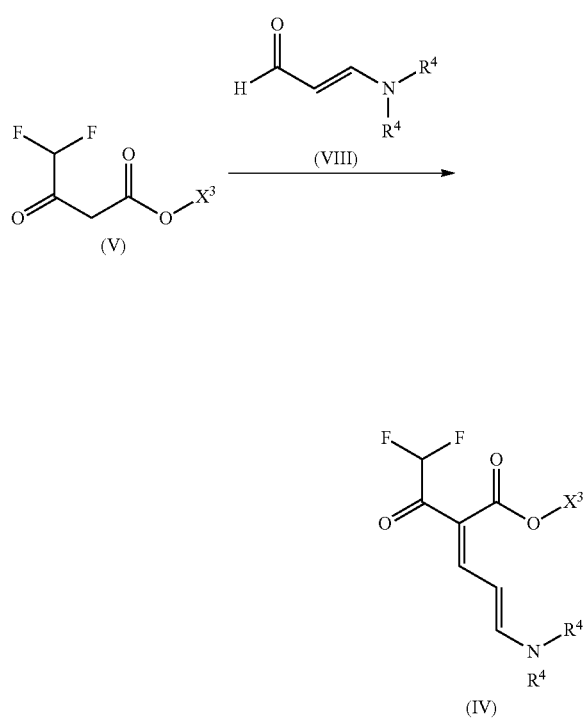

Compounds of formula (III) are obtained when alcohols of formula (IX-a), (IX-b) or (IX-c) are reacted with a catalytic or stoichiometric or super-stoichiometric amount of a Bronsted or Lewis acid and/or a dehydrating agent, optionally in the presence of a diluent (see Process (f)):

Process (f):

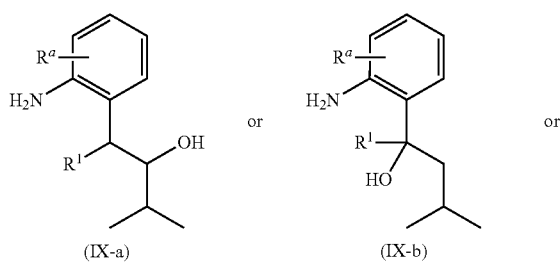

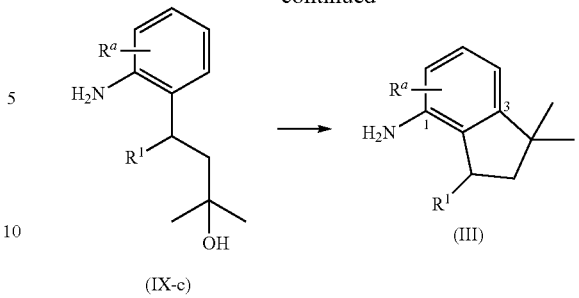

The formulas (IX-a), (IX-b) or (IX-c) provide a general definition of the alcohols required as starting materials for carrying out the Process (e) according to the invention.

In these formulas (IX-a), (IX-b) or (IX-c), $R^a$, $R^1$, $R^2$, $R^3$ have generally, preferably, particularly preferably, very particularly preferably those meanings which have already been mentioned for these radicals in connection with the description of the compounds of the formula (I).

The compounds of formula (IX-a), (IX-b) or (IX-c) can be prepared according to know methods (WO2002/38542, WO2006/120031)

Suitable diluents for carrying out the processes (a), (b), (c), (d), (e) and (f) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexa-methylphosphoric triamide; their mixtures with water or pure water.

The processes (a), (b), (c), (d), (e) and (f) are generally carried out under atmospheric pressure. However, it is also possible to operate under elevated or reduced pressure—in general between 0.1 bar and 100 bar.

When carrying out the processes (a), (b), (c), (d), (e) and (f) according to the invention, the reaction temperatures can be varied within a relatively wide range. In general, the process is carried out at temperatures of from 0° C. to 150° C., preferably at temperatures of from 20° C. to 110° C.

The Process (a) according to the invention is, if appropriate, carried out in the presence of a suitable acid acceptor when $X^3$ represents halogen. Suitable acid acceptors are all customary inorganic or organic bases. These preferably include alkaline earth metal or alkali metal hydrides, hydroxides, amides, alkoholates, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The Process (a) according to the invention is, if appropriate, carried out in the presence of a suitable coupling agent. Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]-phosphorodiamidic chloride, chlorotripyrrolidinophosphonium hexafluorophosphate, bromtripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetramethylene)uronium hexafluorophosphate, O-(1H-benzotriazol-1-yl)-N,N,N',N'-bis(tetramethylene)uronium tetrafluoroborate, N,N,N',N'-bis(tetramethylene)chlorouronium tetrafluoroborate, O-(7-azabenzotriazol-1-yl)-N,N,N,N-tetramethyluronium hexafluorophosphate and 1-hydroxy-benzotriazole. These reagents can be employed separately, but also in combination.

For carrying out the Process (a) according to the invention, in general from 0.2 to 5 mol, preferably from 0.5 to 2 mol, of amine of the formula (III) are employed per mole of the carbonyl halide of formula (XII) or acid of the formula (II). Work-up is carried out by customary methods.

The hydrolysis of the ester may be achieved by standard methods found in the chemical literature, for example, by use of a metal or alkyl ammonium hydroxide in a suitable solvent which may possibly but not necessarily be water or a mixture with water, or by use of alternative bases such as metal carbonates or phosphates in a suitable solvent mixture which includes water.

The Process (e) according to the invention is carried out in the presence of a suitable acid or dehydrating agent. Suitable acid are, for example, HCl, HBr, HF, $H_2SO_4$, $KHSO_4$, AcOH, trifluoroacetic acid, p-toluenesulfonic acid, camphorsulfonic acid, methansulfonic acid, trifluoromethansulfonic acid, polyphosphoric acid, phosphoric acid. Suitable dehydrating agents may be for example carboxylic or sulfonic acid anhydrides.

The Process (f) according to the invention is carried out in the presence of a suitable lewis acid, for example metal halides like $AlCl_3$, $BF_3$, and other lewis acids known in literature; or triflates, for example silver triflate and other triflates described in the literature. The process may also be carried out in the presence of Bronstedt acids like e.g. HCl, HBr, HF, $H_2SO_4$, $KHSO_4$, AcOH, trifluoroacetic acid, p-toluenesulfonic acid, camphorsulfonic acid, methansulfonic acid, trifluoromethansulfonic acid, polyphosphoric acid, and phosphoric acid. Addition of suitable dehydrating agents may be beneficial for this reaction, for example carboxylic or sulfonic acid anhydrides, phosphorous chlorides, aluminium oxide and other agents described in the literature.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to a method for controlling unwanted microorganisms, characterized in that the compounds of the formula (I) are applied to the microorganisms and/or in their habitat.

The invention further relates to seed which has been treated with at least one compound of the formula (I).

The invention finally provides a method for protecting seed against unwanted microorganisms by using seed treated with at least one compound of the formula (I).

The compounds of the formula (I) have potent microbicidal activity and can be used for control of unwanted microorganisms, such as fungi and bacteria, in crop protection and in the protection of materials.

The compounds of the formula (I) have very good fungicidal properties and can be used in crop protection, for example for control of *Plasmodiophoromycetes, Oomycetes, Chytridiomycetes, Zygomycetes, Ascomycetes, Basidiomycetes* and *Deuteromycetes*.

Bactericides can be used in crop protection, for example, for control of Pseudomonadaceae, Rhizobiaceae, Enterobacteriaceae, Corynebacteriaceae and Streptomycetaceae.

The compounds of the formula (I) can be used for curative or protective control of phytopathogenic fungi.

The invention therefore also relates to curative and protective methods for controlling phytopathogenic fungi by the use of the inventive active ingredients or compositions, which are applied to the seed, the plant or plant parts, the fruit or the soil in which the plants grow.

Plants

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Pathogens

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola, Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera, Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora, Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusifomiis, C. paspali, C. africana, Stachybotrys* spec. and others.

Material Protection

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Formulations

The present invention further relates to a composition for controlling unwanted microorganisms, comprising at least one of the compounds of the formula (I). These are preferably fungicidal compositions which comprise agriculturally suitable auxiliaries, solvents, carriers, surfactants or extenders.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The compounds of the formula (I) may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used for controlling unwanted microorganisms, in which the compositions comprising compounds of the formula (I) are applied to the microorganisms and/or in their habitat.

Mixtures

Compounds of the formula (I) can be used as such or in formulations thereof and can be mixed with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals, is also possible.

Seed Treatment

The invention furthermore includes a method for treating seed.

A further aspect of the present invention relates in particular to seeds (dormant, primed, pregerminated or even with emerged roots and leaves) treated with at least one of the compounds of the formula (I). The inventive seeds are used in methods for protection of seeds and emerged plants from the seeds from phytopathogenic harmful fungi. In these methods, seed treated with at least one inventive active ingredient is used.

The compounds of the formula (I) are also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests.

Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient is generally between 0.001 and 15 g per kilogram of seed, preferably between 0.01 and 5 g per kilogram of seed.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

Application Rates

When using the compounds of the formula (I) as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rock-wool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The invention is illustrated by the examples below. However, the invention is not limited to the examples.

PREPARATION EXAMPLES

In analogy to the examples above and according to the general description of the processes of preparing the compounds according to the invention the compounds according to formula (I) in the following Table 1 may be obtained.

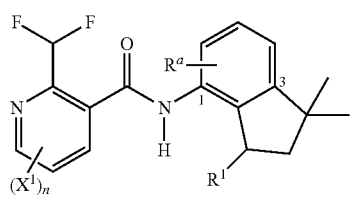

(I)

TABLE 1

| Ex No | n | $X^1$ | $R^a$ | $R^1$ | Log $P^{[a]}$ | |
|---|---|---|---|---|---|---|
| 1 | 0 | H | H | isopropyl | 3.87[a] | |
| 2 | 0 | H | H | ethyl | 3.62[a] | |
| 3 (*) | 0 | H | H | ethyl | 3.62[a] | Enantiomer (−) |
| 4 (*) | 0 | H | H | ethyl | 3.62[a] | Enantiomer (+) |
| 5 | 0 | H | H | propyl | 3.96[a] | |

TABLE 1-continued

| Ex No | n | $X^1$ | $R^a$ | $R^1$ | Log $P^{[a]}$ | |
|---|---|---|---|---|---|---|
| 6 (**) | 0 | H | H | propyl | 3.96[a] | Enantiomer (−) |
| 7 (**) | 0 | H | H | propyl | 3.96[a] | Enantiomer (+) |
| 8 | 1 | 6-chloro | H | propyl | 4.65[a] | |
| 9 | 1 | 5-methyl | H | propyl | 4.25[a] | |
| 10 | 0 | H | H | isobutyl | 4.27[a] | |
| 11 (***) | 0 | H | H | isobutyl | 4.27[a] | Enantiomer (−) |
| 12 (***) | 0 | H | H | isobutyl | 4.27[a] | Enantiomer (+) |
| 13 | 1 | 4-fluoro | H | isobutyl | 4.54[a] | |
| 14 | 1 | 4-fluoro | H | ethyl | 3.87[a] | |
| 15 | 1 | 4-fluoro | H | propyl | 4.21[a] | |

(*) Ex3 and Ex4 are the 2 enantiomers of Ex2
(**) Ex6 and Ex7 are the 2 enantiomers of Ex5
(***) Ex11 and Ex12 are the 2 enantiomers of Ex10

Measurement of Log P values was performed according to EEC directive 79/831 Annex V.A8 by HPLC (High Performance Liquid Chromatography) on reversed phase columns with the following method:

[a] Log P value is determined by measurement of LC-UV, in an acidic range, with 0.1% formic acid in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alka-nones). Lambda-max-values were determined using UV-spectra from 200 nm to 400 nm and the peak values of the chromatographic signals.

In analogy to the examples above and according to the general description of the processes of preparing the compounds according to the invention, the compounds according to formula (III) in the following Table 2 may be obtained

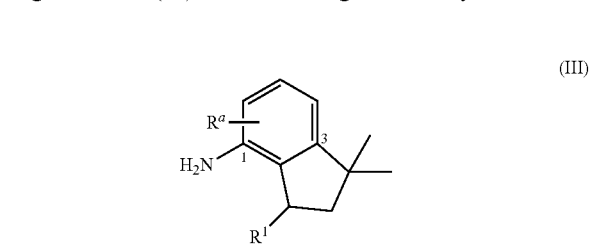

(III)

TABLE 2

| Ex No | $R^a$ | $R^1$ | Log $P^{[a]}$ |
|---|---|---|---|
| III-01 | H | isopropyl | 3.37[a] |
| III-02 | H | ethyl | 2.86[a] |
| III-03 | H | propyl | 3.60[a] |
| III-04 | H | isobutyl | 4.18[a] |

Measurement of Log P values was performed according to EEC directive 79/831 Annex V.A8 by HPLC (High Performance Liquid Chromatography) on reversed phase columns with the following method:

[a] Log P value is determined by measurement of LC-UV, in an acidic range, with 0.1% formic acid in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Example 1

$^1$H-NMR (300.2 MHz, CDCl$_3$): δ=8.825 (1.4); 8.812 (1.4); 8.045 (1.2); 8.020 (1.3); 7.674 (1.4); 7.648 (1.6); 7.606 (1.0); 7.585 (1.5); 7.569 (1.2); 7.544 (0.9); 7.302 (0.9); 7.276 (1.8); 7.270 (1.0); 7.260 (36.4); 7.253 (1.6); 7.251 (1.6); 7.227 (2.1); 7.045 (5.0); 7.024 (1.7); 6.862 (2.0); 3.486 (0.4); 3.461 (0.8); 3.445 (0.9); 3.418 (0.5); 2.317 (0.4); 2.296 (0.7); 2.278 (0.7); 2.256 (0.5); 2.045 (0.5); 1.979 (08); 1.951 (0.9); 1.936 (1.4); 1.907 (1.4); 1.813 (1.5); 1.787 (1.5); 1.769 (1.0); 1.744 (0.9); 1.546 (24.8); 1.373 (16.0); 1.333 (0.4); 1.308 (0.6); 1.267 (3.3); 1.260 (3.0); 1.235 (0.6); 1.189 (9.7); 0-969 (7.6); 0.946 (7.5); 0.904 (1.3); 0.882 (4.2); 0.859 (1.6); 0.689 (11.0); 0.666 (10.8); 0.011 (1.0); 0.000 (39.2); −0.011 (1.8)

Example 2

$^1$H-NMR (400.1 MHz, CDCl$_3$); δ=8.812 (1.2); 8.801 (1.1); 8.073 (0.8); 8.054 (0.9); 7.819 (1.0); 7.799 (1.0); 7.560 (15); 7.517 (0.5) 7.309 (0.6); 7.302 (0.6); 7.283 (1.1); 7.258 (70.0); 7.208 (0.5); 7.158 (1.3); 7.045 (1.7); 7.022 (3.0); 6.995 (0.4); 6.885 (1.3); 3.215 (0.3); 3.190 (0.6); 2.165 (1.1); 2.144 (1.2); 2.133 (1.4); 2.111 (1.3); 2.042 (0.4); 1.825 (1.6); 1.813 (1.5); 1.792 (1.2); 1.780 (1.1); 1.580 (0.4); 1.530 (39.6); 1.500 (0.7); 1.482 (0.7); 1.474 (0.6); 1.465 (0.6); 1.456 (0.6); 1.447 (0.6); 1.439 (0.6); 1.422 (0.5); 1.403 (0.3); 1.343 (16.0); 1.321 (0.5) 1.305 (0.8); 1.285 (1.0); 1.254 (9.1); 0.975 (3.0); 0.957 (6.0); 0.939 (2.8); 0.899 (1.6); 0.882 (5.2); 0.865 (2.2); 0.008 (1.6); 0.000 (52.5); −0.008 (1.8)

Example 3

$^1$H-NMR (400.1 MHz, d$_6$-DMSO); δ=10.302 (3.1); 8.849 (1.9); 8.845 (2.0); 8.837 (2.0); 8.834 (1.9); 8.126 (1.6); 8.107 (1.8); 7.777 (1.3); 7.765 (1.4); 7.757 (1.3); 7.746 (1.2); 7.350 (1.7); 7.274 (0.8); 7.271 (1.1); 7.255 (3.3); 7.251 (3.2); 7.246 (2.6); 7.228 (2.6); 7.214 (4.0); 7.101 (2.2); 7.098 (2.1); 7.084 (2.0); 7.079 (3.1); 5.761 (5.7); 3.380 (1.2) 3.330 (127.3); 2.531 (0.5); 2.518 (11.8); 2.513 (24.0); 2.509 (32.5); 2.504 (22.9); 2.500 (10.7); 2.093 (3.4); 2.072 (1.3); 2.061 (1.6); 2.040 (1.4); 1.916 (0.5); 1.908 (0.5); 1.897 (0.6); 1.889 (0.6); 1.882 (0.7); 1.874 (0.6); 1.864 (0.6); 1.856 (0.5); 1.698 (1.4); 1.683 (1.4); 1.666 (1.3); 1.651 (1.2); 1.363 (0.6); 1.344 (1.0); 1.327 (16.0); 1.304 (0.9); 1.293 (0.4); 1.286 (0.6); 1.248 (0.6): 1.195 (12.7); 0.890 (3.7); 0.871 (7.8); 0.853 (3.4)

Example 4

$^1$H-NMR (400.1 MHz, d$_6$-DMSO): δ=10.301 (3.1); 8.849 (1.9); 8.845 (2.0); 8.837 (2.0); 8.833 (1.9); 8.126 (1.6); 8.106 (1.8); 7.777 (1.3); 7.765 (1.4); 7.758 (1.2); 7.746 (1.1); 7.349 (1.7); 7.273 (0.8); 7.270 (1.1); 7.254 (3.3); 7.250 (3.3); 7.246 (2.7); 7.228 (2.5); 7.213 (3.9); 7.101 (2.2); 7.098 (2.1); 7.084 (1.9); 7.078 (2.5); 5.761 (5.1); 3.429 (0.5); 3.378 (1.3); 3.348 (1.8); 3.328 (296.8); 3.311 (1.6); 3.304 (1.0); 3.278 (1.6); 2.678 (0.4); 2.531 (1.2); 2518 (27.1); 2.513 (54.9); 2.509 (74.1); 2.504 (52.2); 2.500 (24.1); 2.463 (0.4); 2.459 (0.5); 2.454 (0.4); 2.340 (0.3); 2.335 (0.4); 2.331 (0.3); 2.093 (6.0); 2.071 (1.4); 2.060 (1.6); 2.039 (1.4); 1.915 (0.4); 1.907 (0.5); 1.896 (0.6); 1.889 (0.6); 1.882 (0.7); 1.873 (0.6); 1.863 (0.6); 1.855 (0.5); 1.697 (1.4); 1.682 (1.4); 1.665 (1.2); 1.650 (1.2); 1.362 (0.6); 1.344 (1.0); 1.326 (16.0); 1.310 (0.9); 1.303 (0.8); 1.292 (0.4); 1.285 (0.6); 1.194 (12.7); 0.889 (3.7); 0.871 (7.8); 0.852 (3.4)

Example 5

$^1$H-NMR (400.1 MHz, d$_6$-DMSO): δ=10.299 (3.2); 8.853 (1.9); 8.849 (2.0); 8.841 (2.0); 8.838 (1.9); 8.128 (1.6); 8.109 (1.8); 7.788 (1.3) 7.776 (1.4); 7.768 (1.3); 7.756 (1.2); 7.355 (1.7); 7.252 (0.7); 7.239 (6.0); 7.233 (3.4); 7.224 (3.3); 7.219 (4.1); 7.204 (0.7); 7.101 (2.0); 7.095 (1.6); 7.084 (2.6); 7.080 (1.6); 3.405 (0.8); 3.383 (0.8); 3.361 (0.6); 3.311 (70.2); 2.682 (0.3); 2.677 (0.5); 2.563 (0.3): 2.558 (0.4); 2.530 (1.3); 2.517 (27.6); 2.513 (55.9); 2.508 (75.3); 2.503 (52.6); 2.499 (24.2); 2.463 (0.4); 2.458 (0.4);

2.339 (0.3); 2.335 (0.4); 2.330 (0.3); 2.103 (1.2); 2.082 (1.3); 2.071 (1.5); 2.050 (1.3); 1.854 (0.5); 1.847 (0.4); 1.835 (0.5); 1.822 (0.8); 1.813 (0.6); 1.803 (0.5); 1.694 (1.5); 1.680 (1.4); 1.662 (1.3); 1.648 (1.3); 1.408 (0.4); 1.388 (0.7); 1.363 (0.8); 1.324 (16.0); 1.300 (1.2); 1.291 (1.2); 1.272 (1.8); 1.246 (1.4); 1.226 (0.6); 1.194 (12.7); 1.165 (0.3); 0.939 (0.3); 0.873 (3.6); 0.856 (6.4): 0.838 (2.8)

Example 6

$^1$H-NMR (400.1 MHz, d$_6$-DMSO): δ=10.306 (3.3); 8.854 (1.9); 8.850 (2.1); 8.842 (2.1); 8.838 (2.0); 8.129 (1.6); 8.109 (1.9); 7.789 (1.3); 7.777 (1.4); 7.769 (1.3); 7.757 (1.2); 7.355 (1.7); 7.251 (0.8); 7.239 (6.2); 7.232 (3.7); 7.224 (3.5); 7.220 (4.3); 7.205 (0.8); 7.102 (1.9); 7.095 (1.6); 7.087 (2.0); 7.084 (2.6); 5.760 (2.2); 3.422 (2.1); 3.381 (1.0); 3.372 (3.1); 3.360 (0.8); 3.322 (436.7); 3.272 (3.5); 3.223 (0.6); 3.221 (0.4); 2.683 (0.6); 2.678 (0.8); 2.673 (0.6); 2.609 (0.4); 2.563 (0.6); 2.559 (0.8); 2.554 (0.6); 2.531 (2.7); 2.518 (46.8); 2.513 (96.8); 2.509 (133.6); 2.504 (97.8); 2.500 (49.4); 2.464 (2.4); 2.459 (2.3); 2.345 (0.3); 2.340 (0.6); 2.336 (0.8); 2.331 (0.6); 2.103 (1.3); 2.093 (11.6); 2.082 (1.5); 2.071 (1.7); 2.050 (1.4); 1.853 (0.5); 1.846 (0.5); 1.820 (0.9); 1.802 (0.6); 1.693 (1.5); 1.679 (1.5); 1.662 (1.3); 1.647 (1.3); 1.407 (0.4); 1.387 (0.7); 1.363 (0.8); 1.339 (1.3); 1.324 (16.0); 1.299 (1.4); 1.292 (1.2); 1.269 (2.0); 1.245 (1.8); 1.226 (0.7); 1.194 (13.0); 0.873 (3.6); 0.856 (6.5); 0.838 (3.1)

Example 7

$^1$H-NMR (400.1 MHz, d$_6$-DMSO): δ=10.305 (3.4); 8.853 (2.0); 8.850 (2.1); 8.842 (2.1); 8.838 (2.0); 8.129 (1.7); 8.109 (1.9); 7.789 (1.4); 7.777 (1.5); 7.769 (1.3); 7.757 (1.2); 7.355 (1.6); 7.251 (0.7); 7.239 (6.2); 7.232 (3.7); 7.224 (3.6); 7.220 (4.3); 7.205 (0.8); 7.102 (2.0); 7.095 (1.7); 7.087 (2.1); 7.084 (2.6); 5.760 (1.0); 3.422 (1.1); 3.420 (1.0); 3.403 (1.0); 3.373 (4.8); 3.322 (362.0); 3.275 (2.2); 3.271 (0.9); 3.222 (0.7); 2.683 (0.4); 2.678 (0.6); 2.673 (0.5); 2.569 (0.7); 2.564 (1.2); 2.560 (1.4); 2.555 (1.1); 2.550 (0.8); 2.531 (2.8); 2.518 (39.3); 2.513 (79.6); 2.509 (108.3); 2.504 (78.9); 2.500 (40.0); 2.462 (1.8); 2.457 (1.3); 2.453 (0.9); 2.449 (0.7); 2.409 (0.3); 2.340 (0.5); 2.336 (0.7); 2.331 (0.5); 2.103 (1.3); 2.093 (9.3); 2.082 (1.5); 2.071 (1.7); 2.050 (1.4); 1.853 (0.5); 1.846 (0.5); 1.835 (0.6); 1.821 (0.9); 1.802 (0.6); 1.693 (1.4); 1.679 (1.5); 1.661 (1.4); 1.647 (1.3); 1.407 (0.4); 1.388 (0.8); 1.362 (0.9); 1.345 (0.8); 1.324 (16.0); 1.299 (1.4); 1.292 (1.2); 1.269 (2.0); 1.246 (1.8); 1.226 (0.8); 1.194 (13.1); 0.873 (3.7); 0.856 (6.6); 0.838 (3.1)

Example 8

$^1$H-NMR (400.1 MHz, d$_6$-DMSO): δ=10.346 (2.2); 8.206 (2.1); 8.185 (2.5); 7.956 (2.6); 7.935 (2.2); 7.366 (1.7); 7.260 (0.9); 7.243 (4.8); 7.232 (4.4); 7.227 (3.1); 7.207 (1.0); 7.105 (2.3); 7.098 (2.6); 7.089 (1.7); 7.084 (1.6); 3.385 (0.8); 3.378 (0.7); 3.361 (1.1); 3.341 (0.4); 3.311 (74.5); 2.677 (0.4); 2.673 (0.3); 2.562 (0.4); 2.558 (0.5); 2.553 (0.4); 2.530 (1.2); 2.517 (26.3); 2.513 (53.5); 2.508 (72.5); 2.504 (50.8); 2.499 (23.5); 2.458 (0.3); 2.335 (0.4); 2.102 (1.2); 2.081 (1.3); 2.070 (1.6); 2.049 (1.3); 1.821 (0.5); 1.813 (0.5); 1.789 (0.9); 1.770 (0.6); 1.693 (1.5); 1.679 (1.4); 1.661 (1.3); 1.647 (1.3); 1.397 (1.4); 1.386 (0.4); 1.377 (0.8); 1.372 (0.8); 1.358 (0.8); 1.352 (0.8); 1.321 (16.0); 1.289 (1.5); 1.257 (2.7); 1.242 (1.6); 1.220 (0.6); 1.192 (12.9); 0.906 (0.3); 0.884 (0.7); 0.866 (4.8); 0.849 (6.8); 0.831 (2.9)

Example 9

$^1$H-NMR (400.1 MHz, d$_6$-DMSO): δ=10.249 (3.3); 8.691 (2.8); 8.688 (2.9); 7.934 (2.8); 7.313 (1.5); 7.264 (0.6); 7.260 (1.0); 7.245 (3.5); 7.240 (5.3); 7.223 (2.8); 7.203 (1.1); 7.177 (3.5); 7.096 (2.2); 7.092 (2.1); 7.079 (1.9); 7.075 (1.8); 7.041 (1.8); 3.412 (0.5); 3.404 (0.8); 3.383 (0.8); 3.362 (0.6); 3.312 (40.0); 2.531 (0.8); 2.526 (1.2); 2.517 (12.6); 2.513 (26.1); 2.508 (36.0); 2.504 (26.2); 2.499 (13.2); 2.455 (11.1); 2.103 (1.2); 2.082 (1.3); 2.071 (1.6); 2.050 (1.4); 1.862 (0.5); 1.854 (0.5); 1.842 (0.5); 1.835 (1.0); 1.827 (0.8); 1.817 (0.6); 1.810 (0.6); 1.694 (1.5); 1.680 (1.5): 1.662 (1.3); 1.648 (1.3); 1.420 (0.4); 1.414 (0.3): 1.401 (0.8); 1.394 (0.7); 1.382 (0.8); 1.375 (0.9); 1.356 (0.7); 1.348 (0.7); 1.338 (1.0); 1.323 (16.0); 1.296 (1.6); 1.287 (1.5); 1.279 (1.3); 1.265 (2.2); 1.251 (1.8); 1.244 (1.9); 1.233 (0.8); 1.219 (0.7); 1.194 (13.0); 1.163 (0.7); 0.883 (3.9); 0.866 (6.9); 0.848 (3.4)

Example 10

$^1$H-NMR (400.1 MHz, d$_6$-DMSO): δ=10.292 (3.2); 8.857 (2.0); 8.854 (2.2); 8.846 (2.2); 8.842 (2.2); 8.150 (1.7); 8.131 (1.9); 7.792 (1.4); 7.780 (1.5); 7.773 (1.4); 7.761 (1.3); 7.385 (1.6); 7.249 (3.9); 7.232 (2.4); 7.214 (3.0); 7.204 (2.9); 7.201 (3.7); 7.185 (1.4); 7.182 (1.1); 7.113 (2.3); 7.110 (2.7); 7.107 (2.5); 7.092 (1.9); 7.089 (1.9); 3.466 (0.4); 3.452 (0.6); 3.445 (0.8); 3.433 (0.8); 3.424 (0.7); 3.417 (0.5); 3.411 (0.5); 3.404 (0.4); 3.310 (7.1); 2.531 (0.5); 2.526 (0.8); 2.517 (9.8); 2.513 (20.5); 2.508 (28.5); 2.504 (20.9); 2.499 (10.6); 2.459 (0.5); 2.454 (0.3); 2.112 (1.2); 2.091 (1.4); 2.080 (1.6); 2.059 (1.4); 1.996 (0.9); 1.717 (0.4); 1.710 (0.4); 1.691 (2.8); 1.678 (2.8); 1.664 (2.6); 1.659 (2.7); 1.646 (2.1); 1.625 (0.4); 1.349 (0.4); 1.337 (0.7); 1.322 (16.0); 1.288 (0.8); 1.257 (2.7); 1.229 (1.5); 1.210 (14.3); 1.183 (1.3); 1.178 (1.1); 1.166 (0.7); 1.137 (0.5); 0.876 (7.6); 0.867 (7.2); 0.861 (7.4); 0.849 (3.0); 0.842 (7.3); 0.827 (6.6);

Example 11

$^1$H-NMR (400.0 MHz, d$_6$-DMSO): δ=10.301 (3.3); 8.850 (2.0); 8.847 (2.2); 8.838 (2.2); 8.835 (2.1); 8.142 (1.8); 8.123 (2.1); 7.952 (0.7); 7.788 (1.5); 7.776 (1.5); 7.768 (1.4); 7.756 (1.3); 7.377 (1.5); 7.241 (3.8); 7.224 (2.6); 7.206 (2.8); 7.189 (3.5); 7.173 (1.4); 7.104 (3.5); 7.085 (1.9); 3.454 (0.4); 3.432 (0.8); 3.425 (0.9); 3.412 (0.7); 3.404 (0.5); 3.393 (0.4); 3.349 (0.4); 3.320 (130.9); 2.890 (5.3); 2.731 (4.6); 2.674 (0.6); 2.670 (0.7); 2.666 (0.6); 2.505 (87.5); 2.501 (115.8); 2.497 (86.4); 2.332 (0.5); 2.328 (0.7); 2.323 (0.6); 2.101 (1.3); 2.080 (1.4); 2.069 (1.6); 2.048 (1.4); 1.703 (0.4); 1.696 (0.4); 1.679 (2.8); 1.667 (2.8); 1.648 (2.9); 1.635 (2.0); 1.340 (0.3); 1.312 (16.0); 1.236 (0.6); 1.218 (1.3); 1.201 (14.7); 1.167 (0.9); 0.866 (7.0); 0.851 (6.9); 0.830 (7.2); 0.816 (6.6); 0.000 (1.2); −0.093 (0.3)

Example 12

$^1$H-NMR (400.0 MHz, d$_6$-DMSO): δ=10.301 (3.4); 8.847 (2.2); 8.838 (2.2); 8.835 (2.2); 8.142 (1.9); 8.123 (2.1); 7.952 (0.7); 7.787 (1.4); 7.776 (1.5); 7.768 (1.4); 7.756 (1.3); 7.376 (1.5); 7.241 (3.8); 7.224 (2.6); 7.205 (2.8);

7.189 (3.5); 7.173 (1.4); 7.104 (3.5); 7.085 (2.0); 7.083 (1.9); 3.455 (0.4); 3.440 (0.7); 3.433 (0.8); 3.421 (0.9); 3.412 (0.8); 3.321 (137.9); 2.890 (5.0); 2.730 (4.4); 2.674 (0.5); 2.670 (0.7); 2.666 (0.6); 2.523 (1.9); 2.505 (83.2); 2.501 (109.8); 2.496 (82.5); 2.332 (0.5); 2.328 (0.7); 2.323 (0.5); 2.101 (1.3); 2.080 (1.4); 2.069 (1.6); 2.048 (1.4); 1.702 (0.4); 1.695 (0.4); 1.679 (2.8); 1.666 (2.8); 1.648 (2.9); 1.635 (2.0); 1.312 (16.0); 1.236 (0.6); 1.218 (1.3); 1.201 (14.8); 1.166 (0.9); 0.866 (7.1); 0.851 (6.9); 0.830 (7.2); 0.816 (6.6); 0.000 (1.1)

Example 13

$^1$H-NMR (300.2 MHz, CDCl$_3$): δ=8.900 (0.5); 8.883 (0.5); 8.781 (1.9); 8.763 (2.6); 8.745 (1.3); 8.738 (1.3); 7.831 (2.8); 7.805 (2.7); 7.645 (0.4); 7.420 (2.4); 7.330 (3.1); 7.312 (4.4); 7.284 (7.4); 7.269 (13.7); 7.261 (18.1); 7.216 (1.4); 7.209 (1.6); 7.058 (3.3); 7.034 (4.8); 6.949 (0.6); 6.922 (0.6); 6.854 (1.3); 6.847 (1.5); 3.825 (0.4); 3.812 (0.4); 3.301 (1.2); 3.275 (1.8); 2.181 (1.4); 2.152 (2.2); 2.138 (1.9); 2.118 (1.7); 2.060 (0.4); 2.035 (0.5); 2.008 (0.6); 1.832 (2.8); 1.821 (1.9); 1.789 (2.6); 1.777 (2.2); 1.733 (1.7); 1.709 (1.6); 1.627 (1.6); 1.618 (1.4); 1.570 (10.3); 1.487 (1.9); 1.448 (2.2); 1.390 (1.8); 1.369 (2.9); 1.342 (14.6); 1.336 (16.0); 1.276 (14.6); 1.270 (16.0); 1.231 (2.7); 1.196 (0.7); 1.173 (0.5); 1.055 (0.6); 1.019 (1.1); 0.995 (1.7); 0.969 (1.0); 0.913 (10.8); 0.891 (14.9); 0.881 (11.0); 0.866 (7.6); 0.860 (8.0); 0.803 (1.7); 0.781 (1.6); 0.746 (1.7); 0.731 (1.1); 0.724 (1.1); 0.617 (0.4); 0.599 (0.4); 0.007 (8.9); 0.000 (12.2)

Example 14

$^1$H-NMR (300.2 MHz, CDCl$_3$): δ=8.776 (1.3); 8.757 (1.4); 8.750 (1.5); 8.732 (1.3); 7.764 (1.9); 7.739 (2.1); 7.494 (1.1); 7.330 (1.4); 7.312 (2.3); 7.300 (1.6); 7.287 (2.8); 7.282 (1.8); 7.262 (17.8); 7.207 (1.8); 7.069 (2.2); 7.067 (2.2); 7.044 (1.9); 7.042 (1.8); 7.025 (3.7); 6.844 (1.8); 3.213 (0.4); 3.200 (0.5); 3.181 (0.7); 3.165 (0.6); 3.150 (0.5); 3.138 (0.3); 2.175 (1.2); 2.146 (1.2); 2.131 (1.7); 2.103 (1.5); 1.924 (0.5); 1.913 (0.5); 1.900 (0.6); 1.889 (0.6): 1.878 (0.7); 1.867 (0.7); 1.853 (0.7); 1.843 (2.2); 1.828 (1.9); 1.799 (1.4); 1.785 (1.4); 1.599 (1.4); 1.551 (0.4); 1.537 (0.4); 1.512 (0.7); 1.501 (0.4); 1.488 (0.8); 1.477 (0.7); 1.466 (0.8); 1.452 (0.8); 1.442 (0.6); 1.430 (0.7); 1.418 (0.7); 1.403 (1.0); 1.396 (0.8); 1.378 (0.6); 1.365 (0.6); 1.343 (15.9); 1.328 (1.6); 1.319 (0.7); 1.304 (0.6); 1.293 (0.4); 1.259 (16.0); 1.236 (1.0); 1.226 (0.7); 1.199 (0.5); 1.192 (0.5); 1.177 (0.8); 1.148 (0.3); 1.060 (0.4); 1.034 (0.5); 1.029 (0.5); 1.023 (0.4); 0.998 (4.7); 0.974 (8.8); 0.949 (3.7); 0.900 (0.3); 0.885 (0.4); 0.876 (0.6); 0.861 (0.4); 0.852 (0.5); 0.011 (0.3); 0.000 (11.2); −0.011 (0.5)

Example 15

$^1$H-NMR (300.2 MHz, CDCl$_3$): δ=8.776 (1.3); 8.757 (1.4); 8.750 (1.5); 8.732 (1.4); 7.770 (1.9); 7.745 (2.2); 7.486 (1.0); 7.330 (1.3); 7.309 (2.2); 7.301 (1.5); 7.283 (3.6); 7.262 (7.9); 7.259 (1.8); 7.258 (1.8); 7.204 (1.8); 7.064 (2.2); 7.062 (2.3); 7.039 (1.9); 7.037 (1.8); 7.022 (3.8); 6.841 (1.9); 3.265 (0.4); 3.233 (0.7); 3.219 (0.5); 3.203 (0.5); 2.179 (1.1); 2.150 (1.1); 2.135 (1.5); 2.106 (1.4); 1.834 (1.9); 1.820 (2.0); 1.803 (0.8); 1.791 (0.6); 1.777 (1.6); 1.762 (0.6); 1.591 (8.1); 1.521 (0.4); 1.509 (0.4); 1.494 (0.6); 1.487 (0.9); 1.463 (1.2); 1.452 (1.2); 1.429 (1.0); 1.416 (1.0); 1.407 (0.7); 1.385 (1.0); 1.380 (0.9); 1.374 (0.8); 1.359 (0.7); 1.342 (16.0); 1.314 (0.8); 1.290 (0.4); 1.257 (15.7); 0.923 (3.4); 0.900 (7.0); 0.876 (2.9); 0.000 (6.6)

Example 1

$^1$H-NMR (300.2 MHz, CDCl$_3$): δ=8.825 (1.4); 8.812 (1.4); 8.045 (1.2); 8.020 (1.3); 7.674 (1.4); 7.648 (1.6); 7.606 (1.0); 7.585 (1.5); 7.569 (1.2); 7.544 (0.9); 7.302 (0.9); 7.276 (1.8); 7.270 (1.0); 7.260 (36.4); 7.253 (1.6); 7.251 (1.6); 7.227 (2.1); 7.045 (5.0); 7.024 (1.7); 6.862 (2.0); 3.486 (0.4); 3.461 (0.8); 3.445 (0.9); 3.418 (0.5); 2.317 (0.4); 2.296 (0.7); 2.278 (0.7); 2.256 (0.5); 2.045 (0.5); 1.979 (0.8); 1.951 (0.9); 1.936 (1.4); 1.907 (1.4); 1.813 (1.5); 1.787 (1.5); 1.769 (1.0); 1.744 (0.9); 1.546 (24.8); 1.373 (16.0); 1.333 (0.4); 1.308 (0.6); 1.267 (3.3); 1.260 (3.0); 1.235 (0.6); 1.189 (9.7); 0.969 (7.6); 0.946 (7.5); 0.904 (1.3); 0.882 (4.2); 0.859 (1.6); 0.689 (11.0); 0.666 (10.8); 0.011 (1.0); 0.000 (39.2); −0.011 (1.8)

Example 2

$^1$H-NMR (400.1 MHz, CDCl$_3$): δ=8.812 (1.2); 8.801 (1.1); 8.073 (0.8); 8.054 (0.9); 7.819 (1.0); 7.799 (1.0); 7.560 (1.5); 7.517 (0.5); 7.309 (0.6); 7.302 (0.6); 7.283 (1.1); 7.258 (70.0); 7.208 (0.5); 7.158 (1.3); 7.045 (1.7); 7.022 (3.0); 6.995 (0.4); 6.885 (1.3); 3.215 (0.3); 3.190 (0.6); 2.165 (1.1); 2.144 (1.2); 2.133 (1.4); 2.111 (1.3); 2.042 (1.9); 1.825 (1.6); 1.813 (1.5); 1.792 (1.2); 1.780 (1.1); 1.580 (0.4); 1.530 (39.6); 1.500 (0.7); 1.482 (0.7); 1.474 (0.6); 1.465 (0.6); 1.456 (0.6); 1.447 (0.6); 1.439 (0.6); 1.422 (0.5); 1.403 (0.3); 1.343 (16.0); 1.321 (0.5); 1.305 (0.8); 1.285 (1.0); 1.254 (9.1); 0.975 (3.0); 0.957 (6.0); 0.939 (2.8); 0.899 (1.6); 0.882 (5.2); 0.865 (2.2); 0.008 (1.6); 0.000 (52.5); −0.008 (1.8)

Example 3

$^1$H-NMR (400.1 MHz, d$_6$-DMSO); δ=10.302 (3.1); 8.849 (1.9); 8.845 (2.0); 8.837 (2.0); 8.834 (1.9); 8.126 (1.6); 8.107 (1.8); 7.777 (1.3); 7.765 (1.4); 7.757 (1.3); 7.746 (1.2); 7.350 (1.7); 7.274 (0.8); 7.271 (1.1); 7.255 (3.3); 7.251 (3.2); 7.246 (2.6); 7.228 (2.6); 7.214 (4.0); 7.101 (2.2); 7.098 (2.1); 7.084 (2.0); 7.079 (3.1); 5.761 (5.7); 3.380 (1.2); 330 (127.3); 2.531 (0.5); 2.518 (11.8); 2.513 (24.0); 2.509 (32.5); 2.504 (22.9); 2500 (10.7); 2093 3.4); 2.072 (1.3); 2.061 (1.6); 2.040 (1.4); 1.916 (0.5); 1.908 (0.5); 1.897 (0.6); 1.889 (0.6); 1.882 (0.7); 1.874 (0.6); 1.864 (0.6); 1.856 (0.5): 1.698 (1.4); 1.683 (1.4); 1.666 (1.3); 1.651 (1.2); 1.363 (0.6); 1.344 (1.0); 1.327 (16.0); 1.304 (0.9); 1.293 (0.4); 1.286 (0.6): 1.248 (0.6); 1.195 (12.7); 0.890 (3.7); 0.871 (7.8): 0.853 (3.4)

Example 4

$^1$H-NMR (400.1 MHz, d$_6$-DMSO): δ=10.301 (3.1); 8.849 (1.9); 8.845 (2.0); 8.837 (2.0); 8.833 (1.9); 8.126 (1.6); 8.106 (1.8); 7.777 (1.3); 7.765 (1.4); 7.758 (1.2); 7.746 (1.1); 7.349 (1.7); 7.273 (0.8); 7.270 (1.1); 7.254 (3.3); 7.250 (3.3); 7.246 (2.7); 7.228 (2.5); 7.213 (3.9); 7.101 (2.2); 7.098 (2.1); 7.084 (1.9); 7.078 (2.5); 5.761 (5.1); 3.429 (0.5); 3.378 (1.3); 3.348 (1.8); 3.328 (296.8): 3.311 (1.6); 3.304 (1.0); 3.278 (1.6); 2.678 (0.4); 2.531 (1.2); 2.518 (27.1); 2.513 (54.9); 2.509 (74.1); 2.504 (52.2); 2.500 (24.1); 2.463 (1.4); 2.459 (0.5); 2.454 (0.4); 2.340 (0.3); 2.335 (0.4); 2.331 (0.3); 2.093 (6.0); 2.071 (1.4); 2.060 (1.6); 2.039 (1.4); 1.915 (0.4); 1.907 (0.5); 1.896 (0.6);

1.889 (0.6); 1.882 (0.7); 1.873 (0.6); 1.863 (0.6); 1.855 (0.5); 1.697 (1.4); 1.682 (1.4); 1.665 (1.2); 1.650 (1.2); 1.362 (0.6); 1.344 (1.0); 1.326 (16.0); 1.310 (0.9); 1.303 (0.8); 1.292 (0.4); 1.285 (0.6); 1.194 (12.7); 0.889 (3.7); 0.871 (7.8); 0.852 (3.4)

Example 5

$^1$H-NMR (400.1 MHz, $d_6$-DMSO): δ=10.299 (3.2); 8.853 (1.9); 8.849 (2.0); 8.841 (2.0); 8.838 (1.9); 8.128 (1.6); 8.109 (1.8); 7.788 (1.3); 7.776 (1.4); 7.768 (1.3); 7.756 (1.2); 7.355 (1.7); 7.252 (0.7); 7.239 (6.0); 7.233 (3.4); 7.224 (3.3); 7.219 (4.1); 7.204 (0.7); 7.101 (2.0); 7.095 (1.6); 7.084 (2.6); 7.080 (1.6); 3.405 (0.8); 3.383 (0.8); 3.361 (0.6); 3.311 (70.2); 2.682 (0.3); 2.677 (0.5); 2.563 (0.3); 2.558 (0.4); 2.530 (1.3); 2.517 (27.6); 2.513 (55.9); 2.508 (75.3); 2.503 (52.6); 2.499 (24.2); 2.463 (0.4); 2.458 (0.4); 2.339 (0.3); 2.335 (0.4); 2.330 (0.3); 2.103 (1.2); 2.082 (1.3); 2.071 (1.5); 2.050 (1.3); 1.854 (0.5); 1.847 (0.4); 1.835 (0.5); 1.822 (0.8); 1.813 (0.6); 1.803 (0.5); 1.694 (1.5); 1.680 (1.4); 1.662 (1.3); 1.648 (1.3); 1.408 (0.4); 1.388 (0.7); 1.363 (0.8); 1.324 (16.0); 1.300 (1.2); 1.291 (1.2); 1.272 (1.8); 1.246 (1.4); 1.226 (0.6); 1.194 (12.7); 1.165 (0.3); 0.939 (0.3); 0.873 (3.6); 0.856 (6.4); 0.838 (2.8)

Example 6

$^1$H-NMR (400.1 MHz, $d_6$-DMSO): δ=10.306 (3.3); 8.854 (1.9); 8.850 (2.1); 8.842 (2.1); 8.838 (2.0); 8.129 (1.6); 8.109 (1.9); 7.789 (1.3); 7.777 (1.4); 7.769 (1.3); 7.757 (1.2); 7.355 (1.7); 7.251 (0.8); 7.239 (6.2); 7.232 (3.7); 7.224 (3.5); 7.220 (4.3); 7.205 (0.8); 7.102 (1.9); 7.095 (1.6); 7.087 (2.0); 7.084 (2.6); 5.760 (2.2); 3.422 (2.1); 3.381 (1.0); 3.372 (3.1); 3.360 (0.8); 3.322 (436.7); 3.272 (3.5); 3.213 (0.6); 3.221 (0.4); 2.683 (0.6); 1.678 (0.8); 2.673 (0.6); 2.609 (0.4); 2.563 (0.6); 2.559 (0.8); 2.554 (0.6); 2.531 (2.7); 2.518 (46.8); 2.513 (96.8); 2.509 (133.6); 2.504 (97.8); 2.500 (49.4); 2.464 (2.4); 2.459 (2.3); 2.345 (0.3); 2.340 (0.6); 2.336 (0.8); 2.331 (0.6); 2.103 (1.3); 2.093 (11.6); 2.082 (1.5); 2.071 (1.7); 2.050 (1.4); 1.853 (0.5); 1.846 (0.5); 1.820 (0.9); 1.802 (0.6); 1.693 (15); 1.679 (1.5); 1.662 (1.3); 1.647 (1.3); 1.407 (0.4); 1.387 (0.7); 1.363 (0.8); 1.339 (1.3); 1.324 (16.0); 1.299 (1.4); 1.292 (1.2); 1.269 (2.0); 1.245 (1.8); 1.226 (0.7); 1.194 (13.0); 0.873 (3.6); 0.856 (65); 0.838 (3.1)

Example 7

$^1$H-NMR (400.1 MHz, $d_6$-DMSO): δ=10.305 (3.4); 8.853 (2.0); 8.850 (2.1); 8.842 (2.1); 8.838 (2.0); 8.129 (1.7); 8.109 (1.9); 7.789 (1.4); 7.777 (1.5); 7.769 (1.3); 7.757 (1.2); 7.355 (1.6); 7.151 (0.7); 7.239 (6.2); 7.232 (3.7); 7.224 (3.6); 7.220 (4.3); 7.205 (0.8); 7.102 (2.0); 7.095 (1.7); 7.087 (2.1); 7.084 (2.6); 5.760 (1.0); 3.422 (1.1); 3.420 (1.0); 3.403 (1.0); 3.373 (4.8); 3.322 (362.0); 3.275 (2.2); 3.271 (0.9); 3.222 (0.7); 2.683 (0.4); 2.678 (0.6); 2.673 (05); 2.569 (0.7); 2.564 (1.2); 2.560 (1.4); 2.555 (1.1); 2.550 (0.8); 2.531 (2.8); 2.518 (39.3); 2.513 (79.6); 2.509 (108.3); 2.504 (78.9); 2.500 (40.0); 2.462 (1.8); 2.457 (1.3); 2.453 (0.9); 2.449 (0.7); 2.409 (0.3); 2.340 (0.5); 2.336 (0.7); 2.331 (0.5); 2.103 (1.3); 2.093 (9.3); 2.082 (1.5); 2.071 (1.7); 2.050 (1.4); 1.853 (0.5); 1.846 (0.5); 1.835 (0.6); 1.821 (0.9); 1.802 (0.6); 1.693 (1.4); 1.679 (1.5); 1.661 (1.4); 1.647 (1.3); 1.407 (0.4); 1.388 (0.7); 1.362 (0.9); 1.345 (0.8); 1.324 (16.0); 1.299 (1.4); 1.292 (1.2); 1.269 (2.0); 1.246 (1.8); 1.226 (0.8); 1.194 (13.1); 0.873 (3.7); 0.856 (6.6); 0.838 (3.1)

Example 8

$^1$H-NMR (400.1 MHz, $d_6$-DMSO): δ=10.346 (2.2); 8.206 (2.1); 8.185 (2.5); 7.956 (2.6); 7.935 (2.2); 7.366 (1.7); 7.260 (0.9); 7.243 (4.8); 7.232 (4.4); 7.227 (3.1); 7.207 (1.0); 7.105 (2.3); 7.098 (2.6); 7.089 (1.7); 7.084 (1.6); 3.385 (0.8); 3.378 (0.7); 3.361 (1.1); 3.341 (0.4); 3.311 (74.5); 2.677 (0.4); 2.673 (0.3); 2.562 (0.4); 2.558 (0.5); 2.553 (0.4); 2.530 (1.2); 2.517 (26.3); 2.513 (53.5); 2.508 (72.5); 2.504 (50.8); 2.499 (23.5); 2.458 (0.3); 2.335 (0.4); 2.102 (1.2); 2.081 (1.3); 2.070 (1.6); 2.049 (1.3); 1.821 (0.5); 1.813 (0.5); 1.789 (0.9); 1.770 (0.6): 1.693 (1.5); 1.679 (1.4); 1.661 (1.3); 1.647 (1.3); 1.397 (0.4); 1.386 (0.4); 1.377 (0.8); 1.372 (0.8); 1.358 (0.8); 1.352 (0.8); 1.321 (16.0); 1.289 (1.5); 1.257 (2.7); 1.242 (1.6); 1.220 (0.6); 1.192 (12.9); 0.906 (0.3); 0.884 (0.7); 0.866 (4.8); 0.849 (6.8); 0.831 (2.9)

Example 9

$^1$H-NMR (400.1 MHz, $d_6$-DMSO): δ=10.249 (3.3); 8.691 (2.8); 8.688 (2.9); 7.934 (2.8); 7.313 (1.5); 7.264 (0.6); 7.260 (1.0); 7.245 (3.5); 7.240 (5.3); 7.223 (2.8); 7.203 (1.1); 7.177 (3.5); 7.096 (2.2); 7.092 (2.1); 7.079 (1.9); 7.075 (1.8); 7.041 (1.8); 3.412 (0.5); 3.404 (0.8); 3.383 (0.8); 3.362 (0.6); 3.312 (40.0); 2.531 (0.8); 2.526 (1.2); 2.517 (12.6); 2.513 (26.1); 2.508 (36.0); 2.504 (26.2); 2.499 (13.2); 2.455 (11.1); 2.103 (1.2); 2.082 (1.3); 2.071 (1.6); 2.050 (1.4); 1.862 (0.5); 1.854 (0.5); 1.842 (0.5); 1.835 (1.0); 1.827 (0.8); 1.817 (0.6); 1.810 (0.6); 1.694 (1.5); 1.680 (1.5); 1.662 (1.3); 1.648 (1.3); 1.420 (0.4); 1.414 (0.3); 1.401 (0.8); 1.394 (0.7); 1.382 (0.8); 1.375 (0.9); 1.356 (0.7); 1.348 (0.7); 1.338 (1.0); 1.323 (16.0); 1.296 (1.6); 1.287 (1.5); 1.279 (1.3); 1.265 (2.2); 1.251 (1.8); 1.244 (1.9); 1.233 (0.8); 1.219 (0.7); 1.194 (13.0); 1.163 (0.7); 0.883 (3.9); 0.866 (6.9); 0.848 (3.4)

Example 10

$^1$H-NMR (400.1 MHz, $d_6$-DMSO): δ=10.292 (3.2); 8.857 (2.0); 8.854 (2.2); 8.846 (2.2); 8.842 (2.2); 8.150 (1.7); 8.131 (1.9); 7.792 (1.4); 7.780 (1.5); 7.773 (1.4); 7.761 (1.3); 7.385 (1.6); 7.249 (3.9); 7.232 (2.4); 7.214 (3.0); 7.204 (2.9); 7.201 (3.7); 7.185 (1.4); 7.182 (1.1); 7.113 (2.3); 7.110 (2.7); 7.107 (2.5); 7.092 (1.9); 7.089 (1.9); 3.466 (0.4); 3.452 (0.6); 3.445 (0.8); 3.433 (0.8); 3.424 (0.7); 3.417 (0.5); 3.411 (0.5); 3.404 (0.4); 3.310 (7.1); 2.531 (0.5); 2.526 (0.8); 2.517 (9.8); 2.513 (20.5); 2.508 (28.5); 2.504 (20.9); 2.499 (10.6); 2.459 (0.5); 2.454 (0.3); 2.112 (1.2); 2.091 (1.4); 2.080 (1.6); 2.059 (1.4); 1.996 (0.9); 1.717 (0.4); 1.710 (0.4); 1.691 (2.8); 1.678 (2.8); 1.664 (2.6); 1.659 (2.7); 1.646 (2.1); 1.625 (0.4); 1.349 (0.4); 1.337 (0.7); 1.322 (16.0); 1.288 (0.8); 1.257 (2.7); 1.229 (1.5); 1.210 (14.3); 1.183 (1.3); 1.178 (1.1); 1.166 (0.7); 1.137 (0.5); 0.876 (7.6); 0.867 (7.2); 0.861 (7.4); 0.849 (3.0); 0.842 (7.3); 0.827 (6.6)

Example III-01

$^1$H-NMR (300.2 MHz. CDCl$_3$): δ=7.257 (5.7); 7.051 (1.0); 7.048 (1.0); 7.025 (2.0); 7.023 (2.0); 7.000 (1.2); 6.998 (1.2); 6.593 (1.8); 6.591 (1.9): 6.568 (1.6): 6.566 (1.7); 6.482 (2.1); 6.479 (2.1); 6.456 (2.0); 6.453 (1.9); 3.613

(0.9); 3.341 (0.4); 3.326 (0.5); 3.315 (0.8); 3.299 (0.8); 3.288 (0.5); 3.272 (0.5); 2.524 (0.6); 2.509 (0.6); 2.502 (0.8); 2.486 (0.8); 2.479 (0.7); 2.463 (0.6); 1.919 (1.0); 1.890 (1.0); 1.875 (2.0); 1.847 (1.9); 1.776 (1.4); 1.751 (1.4); 1.732 (0.8); 1.707 (0.8); 1.327 (16.0); 1.143 (14.5); 1.012 (8.6); 0.990 (8.5); 0.728 (9.1); 0.705 (9.0); 0.000 (6.2)

Example III-02

$^1$H-NMR (300.2 MHz, CDCl$_3$): δ=7.257 (9.2); 7.061 (1.0); 7.059 (1.1); 7.034 (2.2); 7.010 (1.3); 7.008 (1.3); 6.612 (1.9); 6.610 (1.9); 6.587 (1.7); 6.585 (1.7); 6.510 (2.2); 6.507 (2.1); 6.484 (2.0); 6.481 (1.9); 3.592 (1.4); 3.065 (0.4); 3.051 (0.4); 3.034 (0.6); 3.016 (0.4); 3.002 (0.4); 2.127 (1.1); 2.099 (1.0); 2.084 (1.4); 2.055 (1.5); 2.046 (1.3); 2.032 (0.5); 2.021 (0.5); 2.007 (0.5); 1.996 (0.5); 1.986 (0.6); 1.975 (0.6); 1.961 (0.6); 1.950 (0.5); 1.794 (1.7); 1.780 (1.6); 1.751 (1.3); 1.737 (1.3); 1.547 (1.4); 1.478 (0.5); 1.454 (0.6); 1.444 (0.5); 1.432 (0.6); 1.420 (0.7); 1.408 (0.6); 1.397 (0.6); 1.373 (0.5); 1.304 (15.7); 1.283 (0.6); 1.259 (0.7); 1.236 (0.4); 1.214 (16.0); 1.030 (4.6); 1.005 (9.3); 0.980 (3.9); 0.000 (7.6); −0.011 (0.3)

Example III-03

$^1$H-NMR (300.2 MHz, CDCl$_3$): δ=7.258 (11.3); 7.059 (1.1); 7.057 (1.1); 7.032 (2.3); 7.008 (1.3); 7.006 (1.4); 6.609 (2.0); 6.584 (1.8); 6.512 (2.2); 6.509 (2.2); 6.486 (2.0); 6.483 (2.0); 3.127 (0.4); 3.097 (0.6); 3.086 (0.5); 3.065 (0.4); 2.132 (1.1); 2.103 (1.1); 2.089 (1.5); 2.060 (1.4); 1.935 (0.5); 1.924 (0.4); 1.910 (0.4); 1.899 (0.8); 1.890 (0.7); 1.878 (0.3); 1.867 (0.5); 1.811 (0.4); 1.788 (1.8); 1.774 (1.8); 1.744 (1.4); 1.731 (1.4); 1.564 (0.3); 1.537 (0.7); 1.529 (0.5); 1.512 (0.7); 1.505 (0.7); 1.494 (0.4); 1.480 (0.6); 1.472 (0.5); 1.464 (0.5); 1.460 (0.5); 1.445 (0.4); 1.433 (0.9); 1.422 (0.9); 1.407 (0.6); 1.399 (1.3); 1.391 (1.5); 1.378 (0.7); 1.371 (0.8); 1.361 (1.0); 1.345 (0.5); 1.330 (0.4); 1.303 (15.8); 1.279 (0.6); 1.275 (0.7); 1.247 (0.5); 1.238 (0.4); 1.213 (16.0); 1.092 (0.4); 1.031 (0.5); 1.021 (0.3); 1.007 (0.8); 0.990 (3.3); 0.979 (1.3); 0.967 (5.9); 0.953 (1.2); 0.943 (3.0); 0.915 (0.4); 0.907 (0.5); 0.895 (0.5); 0.888 (0.7); 0.877 (0.5); 0.870 (0.6); 0.866 (0.7); 0.000 (12.5); −0.011 (0.6)

Example III-04

$^1$H-NMR (400.1 MHz, d$_6$-DMSO): δ=6.874 (1.4); 6.855 (2.9); 6.836 (1.6); 6.412 (2.8); 6391 (4.0); 6.371 (2.4); 4.528 (4.5); 3.300 (12.9); 3.118 (0.5); 3.097 (0.9); 3.090 (0.9); 3.082 (0.4); 3.076 (0.4); 3.068 (0.6); 3.061 (0.3); 2.508 (9.1); 2.504 (17.6); 2.499 (23.2); 2.495 (16.6); 2.490 (8.0); 2.001 (1.1); 1.979 (1.2); 1.969 (1.5); 1.947 (1.4); 1.791 (0.4); 1.784 (0.4); 1.767 (1.0); 1.760 (1.3); 1.745 (1.5); 1.735 (1.8); 1.723 (0.8); 1.715 (0.6); 1.707 (0.5); 1.694 (1.9); 1.685 (1.8); 1.661 (1.4); 1.653 (1.4); 1.244 (0.6); 1.233 (0.6); 1.212 (15.7); 1.146 (16.0); 1.115 (1.2); 1.110 (1.2); 1.086 (0.8); 1.062 (0.5); 0.974 (7.4); 0.959 (6.7); 0.941 (0.5); 0.917 (7.3); 0.901 (6.8); 0.859 (0.4); 0.000 (1.4)

EXPERIMENTAL EXAMPLES

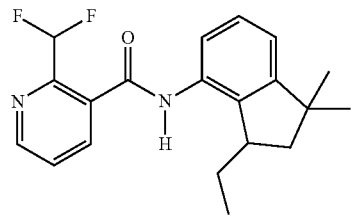 [SMILES: CCC1CC(C)(C)c2cccc(NC(=O)c3cccnc3C(F)F)c21]

To a cold (0° C.) solution of 3-ethyl-1,1-dimethylindan-4-amine (5 g, 26.41 mmol, 1 eq.), DMAP (0.161 g, 1.32 mmol, 0.05 eq.) and TEA (4 g, 5.52 ml, 39.62 mmol, 1.5 eq.) in THF (200 ml) is added dropwise a solution of 2-(difluoromethyl)nicotinoyl chloride (5.56 mmol, 29.05 mmol, 1.1 eq.) in THF (25 ml). Once the addition is complete, the reaction is stirred at room temperature for 3 h. Then the solvent is removed under reduced pressure and the residue is triturated in AcOEt. The solid is removed by filtration and the solution is washed with aq. 1N HCl, 1 N aq. NaOH and brine. The organic phase is dried over MgSO$_4$ and concentrated to give a dark syrup. Purification by chromatography on silica gel gives 2-(difluoromethyl)-N-(3-ethyl-1,1-dimethyl-2,3-dihydro-1H-inden-4-yl)nicotinamide (8.38 g, 68%) as a white solid.

See table 1 for NMR data

To a suspension of 2-(difluoromethyl)nicotinic acid (25 g, 144 mmol, 1 eq.) in DCM (200 ml) is added thionyl chloride (85.9 g, 52.66 ml, 722 mmol, 5 eq.) and DMF (0.1 g, 0.11 ml, 1.44 mmol, 0.01 eq.). The reaction is refluxed for 2 h and further stirred at room temperature overnight. Solvent and excess thionyl chloride are removed under reduced pressure to give 2-(difluoromethyl)nicotinoyl chloride as a yellowish oil (26.5 g, 96%) that was used in the next step without further purification.

$^1$H-NMR (300 MHz, CDCl$_3$): 8.92 (d, 1H); 8.55 (d, 1H); 7.65 (dd, 1H), 7.13 (t, 1H).

To a solution of Ethyl 2-(difluoromethyl)nicotinate (0.1 g, 0.49 mmol, 1 eq.) in EtOH (4 ml) is added 1N aqueous NaOH (0.74 ml, 0.74 mmol, 1.5 eq.). Stirring is allowed overnight and the reaction is concentrated under reduced pressure. The water layer is acidified with aqueous 1N HCl and extracted with AcOEt to give 2-(difluoromethyl)nicotinic acid (82 mg, 95%) as a solid.

$^1$H-NMR (300 MHz, DMSO): 8.85 (d, 1H); 8.32 (d, 1H); 7.70 (dd, 1H); 7.53 (t, 1H).

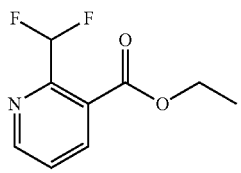

A solution of Ethyl-5-(diethylamino)-2-(difluoracetyl)penta-2,4-dienoate (6.78 g, 24.6 mmol, 1 eq.) in ethanol (30 ml), is heated to reflux, followed by slow addition of ammonium hydroxide (25%-11 ml). After 90 minutes the mixture is cooled to 20° C. and neutralized with diluted aqueous (0.1 M) hydrochloric acid. The majority of ethanol is evaporated and the remaining aqueous layer extracted with AcOEt (3×40 ml). The combined organic layers are dried over MgSO$_4$ and concentrated under reduced pressure to yield Ethyl 2-(difluoromethyl)nicotinate (2.95 g, 60%).

$^1$H-NMR (400 MHz, DMSO): 8.89 (d, 1H); 8.33 (d, 1H); 7.74 (dd, 1H); 7.42 (t, 1H); 4.36 (t, 2H); 1.33 (q, 3H)

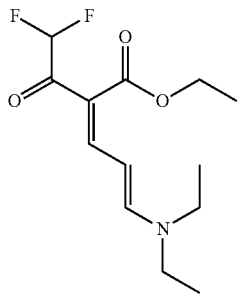 [SMILES: CCOC(=O)/C(=C\C=C\N(CC)CC)C(=O)C(F)F]

To a solution of diethyl formamide (3.3 g, 3 ml, 32.6 mmol, 1.1 eq.) in DCM (45 ml) cooled to 0° C., is slowly added oxalyl chloride (4.5 g, 35.4 mmol, 1.2 eq.). After warming to 20° C. and stirring for further 30 minutes, the mixture is cooled down to 0° C. and n-butyl vinylether (6.0 g, 59 mmol, 2 eq.) is added. After stirring for 2 hours at 20° C., the orange solution is cooled down to 0° C. again, followed by addition of difluoro acetylacetoacetate (5.0 g, 29.5 mmol, 1 eq.) and triethylamine (9.0 g, 88.5 mmol, 3 eq.). The mixture now turns into a red suspension. After stirring for 10 min without cooling, 45 ml of 10% aqueous hydrochloric acid is added. After extraction with dichloromethane (3×45 ml), the combined organic layers are dried (MgSO$_4$) and concentrated under reduced pressure. Addition of hexane (45 ml) yields orange crystals which are isolated by filtration and dried in vacuum to give Ethyl-5-(diethylamino)-2-(difluoracetyl)penta-2,4-dienoate (6.78 g, 83%)

$^1$H-NMR (400 MHz, CDCl$_3$): 7.85 (dd, 1H); 7.26 (m, 2H); 6.75 (t, 1H); 4.26 (q, 2H); 3.43 (m, 4H); 1.32 (m, 9H).

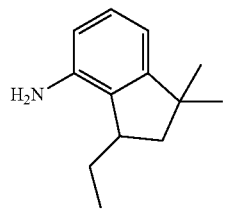

A suspension of 3-(2-aminophenyl)-5-methylhexan-3-ol (0.632 g, 3.04 mmol, 1 eq.) in PPA (5.9 g, 30.48 mmol, 10 eq.) is heated to 80° C. for 3 days. GC-MS shows a total conversion. The reaction is then cooled to r.t. and poured into a solution of ammonium hydroxide (25%) and ice upon vigorous stirring. The mixture is then extracted with AcOEt (3×150 ml), the combined organics are dried over MgSO$_4$ and concentrated under reduced pressure. The residue is purified by chromatography on silica gel to give 3-ethyl-1,1-dimethylindan-4-amine (0.351 g, 52%) as a clear oil.

See table 2 for NMR data

Example: In Vivo Preventive Test on *Alternaria brassicae* (Leaf Spot on Radish)

| Solvent: | 5% by volume of Dimethyl sulfoxide |
| | 10% by volume of Acetone |
| Emulsifier: | 1 μl of Tween ® 80 per mg of active ingredient |

The active ingredients are made soluble and homogenized in a mixture of Dimethyl sulfoxide/Acetone//Tween® 80 and then diluted in water to the desired concentration.

The young plants of radish are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Alternaria brassicae* spores. The contaminated radish plants are incubated for 6 days at 20° C. and at 100% relative humidity.

The test is evaluated 6 days after the inoculation. 0% means an efficacy which corresponds to that of the control plants while an efficacy of 100% means that no disease is observed.

In this test the following compounds according to the invention showed efficacy between 90% and 100% at a concentration of 100 ppm of active ingredient: 1; 2; 3

Example: In Vivo Preventive Test on *Botrytis cinerea* (Grey Mould)

| Solvent: | 5% by volume of Dimethyl sulfoxide |
| | 10% by volume of Acetone |
| Emulsifier: | 1 μl of Tween ® 80 per mg of active ingredient |

The active ingredients are made soluble and homogenized in a mixture of Dimethyl sulfoxide/Acetone//Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 100 ppm of active ingredient: 6; 13

In this test the following compounds according to the invention showed efficacy between 80% and 89% at a concentration of 100 ppm of active ingredient: 3; 15

In this test the following compounds according to the invention showed efficacy between 90% and 100% at a concentration of 100 ppm of active ingredient: 1; 2; 11; 14

Under the same conditions, very good protection is observed at a dose of 100 ppm of active ingredient with compound of example 2, whereas weak protection is observed with compound 11 from EP0256503

| Example | dose (ppm) | Efficacy |
| --- | --- | --- |
| 2 from this patent | 100 | 93 |
| Compound 11 from EP0256503 | 100 | 40 |

Example: In Vivo Preventive Test on *Puccinia recondita* (Brown Rust on Wheat)

| Solvent: | 5% by volume of Dimethyl sulfoxide |
| --- | --- |
| | 10% by volume of Acetone |
| Emulsifier: | 1 µl of Tween® 80 per mg of active ingredient |

The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 100 ppm of active ingredient: 9; 12

In this test the following compounds according to the invention showed efficacy between 80% and 89% at a concentration of 100 ppm of active ingredient: 4; 7

In this test the following compounds according to the invention showed efficacy between 90% and 100% at a concentration of 100 ppm of active ingredient: 1; 2; 3; 5; 6; 8; 10; 11; 13; 14; 15

Example: In Vivo Preventive Test on *Pyrenophora teres* (Net Blotch on Barley)

| Solvent: | 5% by volume of Dimethyl sulfoxide |
| --- | --- |
| | 10% by volume of Acetone |
| Emulsifier: | 1 µl of Tween® 80 per mg of active ingredient |

The active ingredients are made soluble and homogenized in a mixture of Dimethyl sulfoxide/Acetone//Tween® 80 and then diluted in water to the desired concentration.

The young plants of barley are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Pyreoophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test the following compounds according to the invention showed efficacy between 70% and 79% at a concentration of 100 ppm of active ingredient: 5

In this test the following compounds according to the invention showed efficacy between 80% and 89% at a concentration of 100 ppm of active ingredient: 1; 3; 11

In this test the following compounds according to the invention showed efficacy between 90% and 100% at a concentration of 100 ppm of active ingredient: 2; 6

Under the same conditions, very good protection is observed at a dose of 100 ppm and moderate protection is observed at a dose of 10 ppm of active ingredient with compound of example 2, whereas moderate protection is observed at 100 ppm and no protection at all is observed at 10 ppm with 2-chloro-N-(3-ethyl-1,1-dimethyl-2,3-dihydro-1H-inden-4-yl)nicotinamide and no protection at all is observed at both dose rates with compound 11 from EP0256503

| Example | dose (ppm) | Efficacy |
| --- | --- | --- |
| 2 from this patent | 100 | 93 |
| 2 from this patent | 10 | 64 |
| 2-chloro-N-(3-ethyl-1,1-dimethyl-2,3-dihydro-1H-inden-4-yl)nicotinamide | 100 | 71 |
| 2-chloro-N-(3-ethyl-1,1-dimethyl-2,3-dihydro-1H-inden-4-yl)nicotinamide | 10 | 0 |
| Compound 11 from EP0256503 | 100 | 0 |
| Compound 11 from EP0256503 | 10 | 0 |

Example: In Vivo Preventive Test on *Septoria tritici* (Leaf Spot on Wheat)

| Solvent: | 5% by volume of Dimethyl sulfoxide |
| --- | --- |
| | 10% by volume of Acetone |
| Emulsifier: | 1 µl of Tween® 80 per mg of active ingredient |

The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy between 80% and 89% at a concentration of 100 ppm of active ingredient: 11; 14

In this test the following compounds according to the invention showed efficacy between 90% and 100% at a concentration of 100 ppm of active ingredient: 2

Under the same conditions, very good protection is observed at a dose of 10 ppm of active ingredient with compound of example 2, whereas only moderate protection is observed with 2-chloro-N-(3-ethyl-1,1-dimethyl-2,3-dihydro-1H-inden-4-yl)nicotinamide and compound 11 from EP0256503

| Example | dose (ppm) | Efficacy |
| --- | --- | --- |
| 2 from this patent | 10 | 97 |
| 2-chloro-N-(3-ethyl-1,1-dimethyl-2,3-dihydro-1H-inden-4-yl)nicotinamide | 10 | 50 |
| Compound 11 from EP0256503 | 10 | 43 |

Example: In Vivo Preventive Test on *Sphaerotheca fuliginea* (Powdery Mildew on Cucurbits)

| Solvent: | 5% by volume of Dimethyl sulfoxide |
| --- | --- |
| | 10% by volume of Acetone |
| Emulsifier: | 1 µl of Tween ® 80 per mg of active ingredient |

The active ingredients are made soluble and homogenized in a mixture of Dimethyl sulfoxide/Acetone//Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy between 90% and 100% at a concentration of 100 ppm of active ingredient: 1; 2; 3; 5; 6; 10; 11; 13; 15

Under the same conditions, total protection is observed at a dose of 10 ppm of active ingredient with compound of example 2, whereas weak protection is observed with 2-chloro-N-(3-ethyl-1,1-dimethyl-2,3-dihydro-1H-inden-4-yl)nicotinamide and medium protection is observed with compound 11 from EP0256503

| Example | dose (ppm) | Efficacy |
| --- | --- | --- |
| 2 from this patent | 10 | 100 |
| 2-chloro-N-(3-ethyl-1,1-dimethyl-2,3-dihydro-1H-inden-4-yl)nicotinamide | 10 | 44 |
| Compound 11 from EP0256503 | 10 | 89 |

Example: In Vivo Preventive Test on *Uromyces appendiculatus* (Bean Rust)

| Solvent: | 5% by volume of Dimethyl sulfoxide |
| --- | --- |
| | 10% by volume of Acetone |
| Emulsifier: | 1 µl of Tween ® 80 per mg of active ingredient |

The active ingredients are made soluble and homogenized in a mixture of Dimethyl sulfoxide/Acetone//Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 100 ppm of active ingredient: 4

In this test the following compounds according to the invention showed efficacy between 90% and 100% at a concentration of 100 ppm of active ingredient: 1; 2; 3; 5; 6; 8; 10; 11; 13; 14; 15

Example: In Vivo Preventive Test on *Corynespora* Test (Tomatoes)

| Solvent: | 24.5 parts by weight of acetone |
| --- | --- |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Corynespora cassiicola*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed.

In this test the following compounds according to the invention showed efficacy between 90% and 100% at a concentration of 250 ppm of active ingredient: 2; 3; 5

Example: In Vivo Preventive Test on *Phakopsora* Test (Soybeans)

| Solvent: | 24.5 parts by weight of acetone |
| --- | --- |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy between 90% and 100% at a concentration of 10 ppm of active ingredient: 2; 3; 5; 6; 10

Example: In Vivo Preventive Test on *Venturia* Test (Apples)

| Solvent: | 24.5 parts by weight of acetone |
| --- | --- |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy between 90% and 100% at a concentration of 100 ppm of active ingredient: 2; 3; 5; 6

Example: In Vivo Preventive *Fusarium culmorum* Test (Wheat)

| Solvent: | 49 parts by weight of N,N-dimethylacetamide |
| --- | --- |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are slightly injured by using a sandblast and afterwards they are sprayed with a conidia suspension of *Fusarium culmorum*.

The plants are placed in the greenhouse under a translucent incubation cabinet at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed efficacy between 90% and 100% at a concentration of 100 ppm of active ingredient: 2; 3; 6

Example: In Vivo Preventive *Septoria tritici* Test (Wheat)

| Solvent: | 49 parts by weight of N,N-dimethylacetamide |
| --- | --- |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

In this test the following compounds according to the invention showed efficacy between 70% and 79% at a concentration of 100 ppm of active ingredient: 5

In this test the following compounds according to the invention showed efficacy between 90% and 100% at a concentration of 100 ppm of active ingredient: 2; 3; 6

The invention claimed is:

1. A difluoromethyl-nicotinic indanyl carboxamide of formula (I),

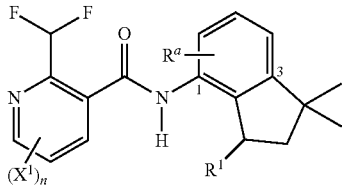

wherein
$X^1$ represents fluorine, chlorine, bromine, methyl, ethyl, trifluoromethyl, or difluoromethyl;
n represents 0 or 1;
$R^a$ represents hydrogen, fluorine, chlorine, bromine, methyl or trifluoromethyl; and
$R^1$ represents ethyl, n-propyl, iso-propyl, or iso-butyl.

2. The difluoromethyl-nicotinic indanyl carboxamide of formula (I) according to claim 1, wherein
n represents 0;
$R^a$ represents hydrogen; and
$R^1$ represents ethyl, n-propyl, iso-propyl, or iso-butyl.

3. The difluoromethyl-nicotinic indanyl carboxamide of formula (I) according to claim 1, wherein the isomers' specific rotation is (−).

4. A compound of formula (III),

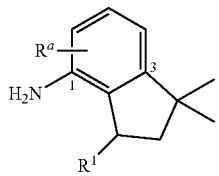

wherein
$R^a$ represents fluorine, chlorine, bromine, methyl or trifluoromethyl; and
$R^1$ represents ethyl, n-propyl, iso-propyl, or iso-butyl.

5. The compound of formula (III) according to claim 4, wherein
$R^1$ represents n-propyl, iso-propyl, or iso-butyl.

6. A compound of formula (IV),

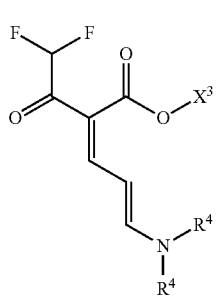

wherein
$X^3$ represents $C_1$-$C_6$ alkyl; and
$R^4$ independently of one another represent $C_1$-$C_6$ alkyl.

7. The compound of formula (IV) according to claim 6, wherein
$X^3$ represents ethyl or methyl; and
$R^4$ independently of one another represent methyl or ethyl.

8. The compound of formula (IV) according to claim 6, wherein
$X^3$ represents ethyl; and
$R^4$ represents ethyl.

9. A composition for controlling phytopathogenic harmful fungi, comprising a content of at least one compound of formula (I) according to claim 1, in addition to one or more extenders and/or surfactants.

10. A method for controlling phytopathogenic harmful fungi, comprising applying one or more compounds of formula (I) according to claim 1 to the phytopathogenic harmful fungi and/or a habitat thereof.

11. A process for producing a composition for controlling phytopathogenic harmful fungi, comprising mixing one or more compounds of formula (I) according to claim 1 with one or more extenders and/or surfactants.

12. A method for controlling phytopathogenic harmful fungi, comprising applying one or more compounds of formula (I) according to claim 1 to transgenic plants, and seeds of transgenic plants.

* * * * *